(12) United States Patent
Bhosale et al.

(10) Patent No.: US 10,766,934 B2
(45) Date of Patent: Sep. 8, 2020

(54) GENETICALLY MODIFIED MICROALGAE

(71) Applicant: RELIANCE INDUSTRIES LIMITED, Mumbai (IN)

(72) Inventors: Manoj Bhosale, Jalgaon (IN); Gautam Das, Adilabad (IN); Tuhin Maity, Kolkata (IN); Pranali Deore, Panvel (IN); Venkatesh Prasad, Bangalore (IN); Santanu Dasgupta, Mumbai (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 70 days.

(21) Appl. No.: 16/086,923

(22) PCT Filed: Mar. 10, 2017

(86) PCT No.: PCT/IB2017/051414
§ 371 (c)(1),
(2) Date: Sep. 20, 2018

(87) PCT Pub. No.: WO2017/163144
PCT Pub. Date: Sep. 28, 2017

(65) Prior Publication Data
US 2019/0106465 A1    Apr. 11, 2019

(30) Foreign Application Priority Data

Mar. 20, 2016 (IN) .............................. 201621003397

(51) Int. Cl.
| | | |
|---|---|---|
| *C07K 14/405* | (2006.01) | |
| *C12N 15/82* | (2006.01) | |
| *C12N 15/79* | (2006.01) | |
| *C12N 1/12* | (2006.01) | |

(52) U.S. Cl.
CPC .............. *C07K 14/405* (2013.01); *C12N 1/12* (2013.01); *C12N 15/79* (2013.01); *C12N 15/82* (2013.01)

(58) Field of Classification Search
CPC ..................................................... C07K 14/405
USPC ........................................................... 435/470
See application file for complete search history.

(56) References Cited

U.S. PATENT DOCUMENTS

2013/0109098 A1    5/2013    Allnutt et al.

FOREIGN PATENT DOCUMENTS

| WO | WO2011140601 | * 11/2011 |
|---|---|---|
| WO | 2015111075 A2 | 7/2015 |

OTHER PUBLICATIONS

Moharikar et al. "A homologue of the defender against the apoptotic death gene (dad1) in UV-exposed Chlamydomonas cells is downregulated with the onset of programmed cell death" J. Biosci. 32(2), (2007), 261-270.
International Search Report issued for international patent application No. PCT/IB2017/051414, dated Jun. 9, 2017.
Written Opinion of the International Searching Authority issued for international patent application No. PCT/IB2017/051414, dated Jun. 9, 2017.

* cited by examiner

*Primary Examiner* — Li Zheng
(74) *Attorney, Agent, or Firm* — Westman, Champlin & Koehler, P.A.

(57) ABSTRACT

The present disclosure provides genetically modified *Chlorella sorokiniana*. DAD1 gene is overexpressed in wild type *Chlorella sorokiniana* to obtain the genetically modified *Chlorella sorokiniana*. The genetically modified *Chlorella sorokiniana* is characterized by increased biomass, increased carrying capacity, reduced clumping, and increased stress tolerance to ultraviolet light and high light intensity, as compared to the wild type *Chlorella sorokiniana*. The genetically modified *Chlorella sorokiniana* can be used for the production of industrially important products.

8 Claims, 5 Drawing Sheets
Specification includes a Sequence Listing.

GENETICALLY MODIFIED MICROALGAE

CROSS-REFERENCE TO RELATED APPLICATION

This application is a Section 371 National Stage Application of International Application No. PCT/IB2017/051414, filed Mar. 10, 2017, and published as WO2017/163144 A1 on Sep. 28, 2017, which claims priority to and benefits of Indian Patent Application Serial No. 201621003397, filed Mar. 20, 2016, the entire contents of which are incorporated herein by reference.

FIELD

The present disclosure relates to genetically modified microalgae.

Definitions

As used in the present disclosure, the following terms are generally intended to have the meaning as set forth below, except to the extent that the context in which they are used indicates otherwise.

Defender against Apoptotic Death 1 (DAD1 gene): Defender against Apoptotic Death 1 is a negative regulator of programmed cell death.

Carrying capacity: Carrying capacity is the maximum population size of a species possible in a given environment without gross changes in the cellular integrity or morphology. It is the ability of an organism to sustain indefinitely, leading to maximum load of the organism possible in a given environment.

Clumping: Some species of algae and bacteria grow in clumps covered in a gelatinous coating allowing them to stick together into large surface scums. This undesirable aggregation of single cells into clumps causes cell death and decrease in vitality of the cells.

Stress tolerance: The term "stress tolerance" refers to the ability of an organism to overcome the negative impact of various biotic and abiotic stresses, such as damage done by other living organisms, nutrient deprivation, photo-oxidative damage caused by UV light and high light intensity, etc.

High light intensity: The term "high light intensity" refers to light having intensities above 80 $\mu Em^2 \, s^{-1}$.

BACKGROUND

Programmed cell death (PCD) also known as apoptosis is characterized by the organized self-destruction of individual cells that may pose a threat to the integrity of the group. It is a well conserved evolutionary trait in both plants and animals alike. This behavior is triggered by a number of environmental stresses, both biotic as well as abiotic components. For example, in large-scale cultivation, algae experience a number of stresses, including nutrient deprivation and photo oxidative damage, which reduce the cell viability.

During commercial cultivation in bioreactors or open ponds, the organism encounters, and is generally able to cope with, many stresses. In certain cases of large-scale cultivation, the organisms die due to PCD as a result of stress, such as, nutrient limitation and the like.

Although PCD is an important natural mechanism for quality control but certain biotechnological production processes favor quantity of biomass yield over quality. Such processes require mass-cultivation of the organism with minimal casualties. One such example of a process that favors quantity of biomass yield over quality is biofuel production from algae. With progression toward inexpensive algal biomass production systems, it is expected that minimal control of culture conditions may lead to increased algal casualities. The development of algal strains better suited to survive conditions of deleterious stress, particularly photo oxidative stress caused by intense light, could have a significant impact on the commercialization of mass-cultured transgenic algae.

Moreover, in such processes where quantity of biomass yield is favored over quality which require the cultivation of algae, it is desirable to have reduced clumping of the algae. Algae has a tendency to form clumps while growing; such clumps restrict the growth of algae, further leading to death via PCD, leading to decrease in the biomass quantity.

There is, therefore, felt a need for a method for reducing clumping and increasing the biomass of an organism.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide genetically modified *Chlorella sorokiniana*.

Still another object of the present disclosure is to provide genetically modified *Chlorella sorokiniana* which is obtained by overexpressing SEQ ID NO. 1 obtained from DAD1 gene in wild type *Chlorella sorokiniana*.

Yet another object of the present disclosure is to provide genetically modified *Chlorella sorokiniana* which exhibits increased biomass, increased carrying capacity, reduced clumping, and increased stress tolerance to ultraviolet light and high light intensity as compared to the wild type *Chlorella sorokiniana*.

Still another object of the present disclosure is to provide a method of genetically modifying *Chlorella sorokiniana*.

Other objects and advantages of the present disclosure will be more apparent from the following description, which is not intended to limit the scope of the present disclosure.

SUMMARY

The present disclosure provides genetically modified *Chlorella sorokiniana* having Accession Number CCAP211/132. The genetically modified *Chlorella sorokiniana* is obtained by overexpressing SEQ ID NO. 1 obtained from DAD1 gene in wild type *Chlorella sorokiniana*. The genetically modified *Chlorella sorokiniana* is characterized by increased biomass, increased carrying capacity, reduced clumping, and increased stress tolerance to ultraviolet light and high light intensity, as compared to that of the wild type *Chlorella sorokiniana*. In one embodiment, the DAD1 gene is obtained from *Chlamydomonas reinhardtii* NW_001843471, from which the sequence as set forth in SEQ ID NO. 1 is identified and is then codon optimized for *Chlorella sorokiniana*.

The present disclosure further provides a method of genetically modifying wild type *Chlorella sorokiniana*. The method comprises cloning SEQ ID NO. 1, obtained from DAD1 gene from *Chlamydomonas reinhardtii* NW_001843471, in a vector, and introducing the vector containing the SEQ ID NO. 1 into wild type *Chlorella sorokiniana* and growing on a medium containing a selective agent under conducive conditions to facilitate the overexpression of sequence (SEQ ID NO. 1), to obtain the genetically modified *Chlorella sorokiniana* having Accession Number CCAP211/132.

BRIEF DESCRIPTION OF THE ACCOMPANYING DRAWING

The present disclosure will now be described with the help of the accompanying drawing, in which.

DETAILED DESCRIPTION

A cell initiates intracellular apoptotic signaling in response to stress, which induces apoptosis, i.e., cell death. Apoptosis is a process of programmed cell death wherein biochemical events lead to characteristic morphological cell changes, eventually death. The biotic and abiotic components, in combination or alone, induce stress which leads to signaling of the programmed cell death. Lack of nutrients in the environment is also a cause for inducing stress. Such a scenario may occur due to increase in the population of that organism, leading to utilization of the nutrients followed by scarcity of the nutrients and eventually inducing stress. In processes that favor quantity of biomass yield over quality, such programmed cell death which causes a loss in the biomass is undesirable.

Accordingly, there exists a need to develop a solution for mitigating the above mentioned drawbacks.

The present disclosure envisages genetically modified microorganism that is characterized by increased biomass, increased carrying capacity, reduced clumping, and increased stress tolerance to ultraviolet light and high light intensity, as compared to that of the wild type *Chlorella sorokiniana*. The present disclosure further provides a method of genetically modifying microorganisms.

In an aspect of the present disclosure, there is provided genetically modified *Chlorella sorokiniana*. The genetically modified *Chlorella sorokiniana* has been deposited at Culture Collection of Algae and protozoa, UK (CCAP) on Jan. 27, 2017 and has been assigned the Accession Number CCAP 211/132.

In one embodiment, the genetically modified *Chlorella sorokiniana* is obtained by overexpressing SEQ ID NO. 1, obtained from the DAD1 gene, in wild type *Chlorella sorokiniana*. Typically, the DAD1 gene is isolated from algae. In another embodiment, the DAD1 gene obtained from *Chlamydomonas reinhardtii* NW_001843471 from which the sequence as set forth in SEQ ID NO. 1 is identified and then is codon optimized for *Chlorella sorokiniana* and is artificially synthesized.

The Defender against Apoptotic Death 1 (DAD1) gene will be henceforth referred to as dad1. The DAD1 gene is an oligosaccharyl transferase involved in N-linked glycosylation. The expression of SEQ ID NO. 1 decreases cell death because of which it can be considered as a universal negative regulator of cell death.

In another aspect of the present disclosure, there is a provided a method of genetically modifying wild type *Chlorella sorokiniana*. The method involves the isolation of the gene of interest from a suitable host and expressing the gene of interest in the desired organism.

Initially, at least one copy of SEQ ID NO. 1 is cloned in a vector. Typically, SEQ ID NO. 1 is obtained from the DAD1 gene of *Chlamydomonas reinhardtii* and is codon optimized for *Chlorella sorokiniana*. In one embodiment, the SEQ ID NO. 1 is artificially synthesized. In one embodiment, dad1 is obtained from *Chlamydomonas reinhardtii* NW_001843471.

In one embodiment, the vector is pChlamy_1.

In the next step, the vector is cloned in wild type *Chlorella sorokiniana* (Gagva, Gujarat, India). Cloning of SEQ ID NO. 1 into the wild type *Chlorella sorokiniana* can be carried out by a technique selected from the group consisting of transposon-mediated insertion, electroporation, magnetophoresis, microinjection, particle inflow gun bombardment, transfection, heat shock transfection, nucleofection transfection, delivery via liposomes, and microinjection.

The vector containing at least one copy of SEQ ID NO. 1 is then introduced into wild type *Chlorella sorokiniana* and grown on a medium containing a selective agent under conducive conditions to facilitate the overexpression of SEQ ID NO. 1 to obtain the genetically modified *Chlorella sorokiniana*. The genetically modified *Chlorella sorokiniana* has been deposited at Culture Collection of Algae and protozoa, UK (CCAP) on Jan. 27, 2017 and has been assigned the Accession Number CCAP 211/132.

In one embodiment, the selective agent is hygromycin.

The genetically modified *Chlorella sorokiniana* CCAP 211/132 of the present disclosure is characterized by increased carrying capacity, reduced clumping between the *Chlorella sorokiniana* cells, and increased biomass as compared to the wild type *Chlorella sorokiniana*. Further, the genetically modified *Chlorella sorokiniana* exhibits increased stress tolerance to ultraviolet light and high light intensity as compared to the wild type *Chlorella sorokiniana*.

The present disclosure is further described in light of the following laboratory scale experiments which are set forth for illustration purpose only and not to be construed for limiting the scope of the disclosure. These laboratory scale experiments can be scaled up to industrial/commercial scale and the results obtained can be extrapolated to industrial/commercial scale.

EXPERIMENTAL DETAILS

Experiment-1: Overexpressing SEQ ID NO. 1 in Wild Type *Chlorella sorokiniana*

Figure 1:
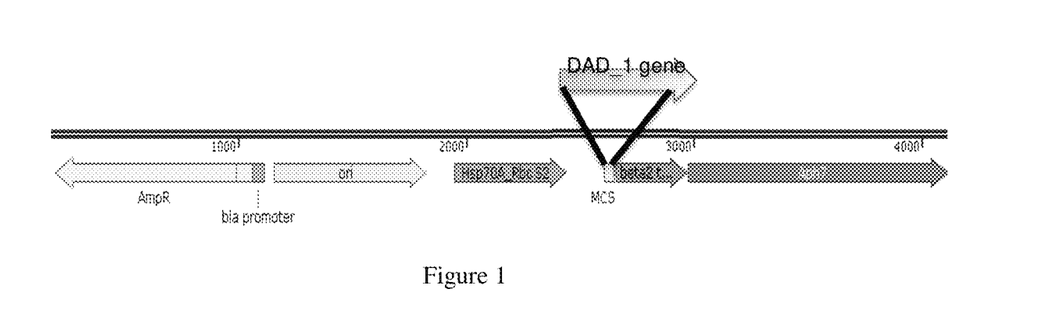
FIG. 1 illustrates a linear map of the SEQ ID NO. 1 from DAD1 gene cloned in the vector-pChlamy_1.

Wild type *Chlorella sorokiniana* (Gagva, Gujarat, India) was grown on a Kuhner shaker (100 rpm) for 14 days, in the presence of 2% ambient $CO_2$. The temperature was maintained at 27° C. The wild type *Chlorella sorokiniana* (Gagva, Gujarat, India) were genetically modified by overexpressing the SEQ ID NO. 1, obtained from dad1 of *Chlamydomonas reinhardtii* having the Accession Number NW_001843471. The SEQ ID NO. 1, was codon optimized for *Chlorella sorokiniana* and was artificially synthesized. pChlamy_1 plasmid was used as the vector for transformation. FIG. 1 illustrates a linear map of the SEQ ID NO. 1 cloned pChlamy_1. It is seen from FIG. 1 that SEQ ID NO. 1 was cloned into multiple cloning site (MCS) (Kpn-I and Nde-I) of pChlamy_1. The gene expression was driven by HSP70-Rbc S2 promoter. Aph7 (Hygromycin) cassette for eukaryotic selection was used.

The electroporation conditions are summarized in Table-1.

TABLE 1

Electroporation conditions

| | |
|---|---|
| Reagent | Max efficiency reagent (Invitrogen) |
| Volts | 1800 v |
| Capacitance | 25 µF |
| Resistance | 200 Ω |
| Cuvette | 2 mm (BioRad) |
| Media | TAP, TAP with 40 mM sucrose for recovery |
| Selection | Hygromycin 50 µg/ml |

The preliminary screening of the genetically modified *Chlorella sorokiniana* was performed using culture polymerase chain reaction (PCR) using supernatant of crude cell lysate as template.

The genetically modified *Chlorella sorokiniana* showing expected size amplification was further up-scaled for gDNA isolation.

The colonies of the genetically modified *Chlorella sorokiniana* were deposited at Culture Collection of Algae and protozoa, UK (CCAP) and have been assigned the Accession Number CCAP 211/132. The genetically modified *Chlorella sorokiniana* CCAP 211/132 were used for further studies.

Figure 2A:
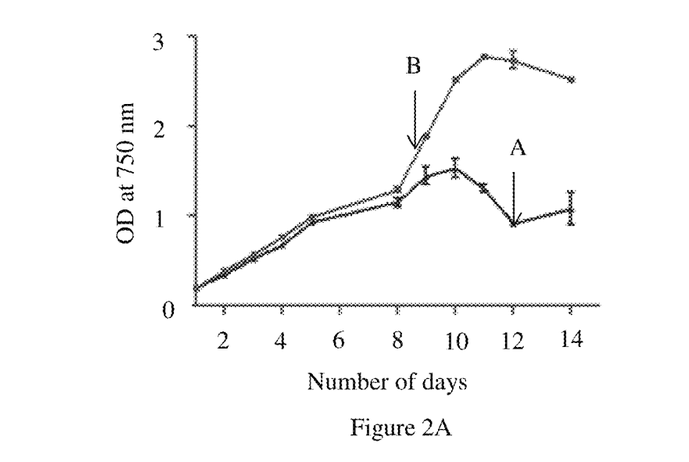
FIG. 2A represents a graph displaying the comparison of the growth curve of wild type *Chlorella sorokiniana* and genetically modified *Chlorella sorokiniana* CCAP 211/132, grown in 4% Salt urea phosphoric acid medium.
Figure 2B:
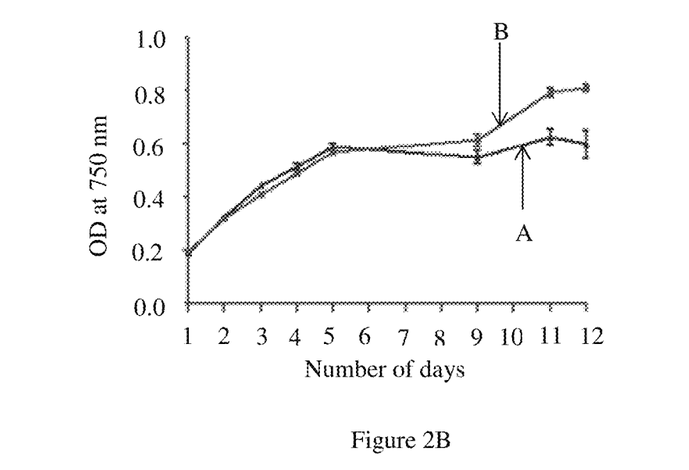
FIG. 2B represents a graph displaying the comparison of the growth curve of wild type *Chlorella sorokiniana* and genetically modified *Chlorella sorokiniana* CCAP 211/132, grown in 4% Salt UPA, 450 µE light (Percival growth chamber)

Studies were carried out to study the effect of overexpression of SEQ ID NO. 1 in *Chlorella sorokiniana*. Cultures of wild type *Chlorella sorokiniana* and the genetically modified *Chlorella sorokiniana* CCAP 211/132 were grown in Kuhner shaker (25° C., 67% humidity, 2% $CO_2$ and 100 rpm) in 4% Salt urea phosphoric acid (UPA) medium were transferred to 4% Salt UPA in Kuhner shaker and 4% Salt UPA in Percival growth chamber (2% $CO_2$ and 450 µE light, 70% humidity). The growth was monitored for about 2 weeks. The results obtained are illustrated in FIG. 2A and FIG. 2B, wherein line-A represents the wild type *Chlorella sorokiniana* and line-B represents the genetically modified *Chlorella sorokiniana* CCAP 211/132. It is seen from FIG. 2A that from day 8 onwards there is an increased growth the genetically modified *Chlorella sorokiniana* CCAP 211/132 (overexpressed with SEQ ID NO. 1) as compared to that of the wild type *Chlorella sorokiniana*, when the cultures were grown in 4% Salt UPA medium. Similarly, an increased growth was observed for the genetically modified *Chlorella sorokiniana* CCAP 211/132 (overexpressed with SEQ ID NO. 1) as compared to the wild type *Chlorella sorokiniana*, when the cultures were grown in 4% Salt UPA 450 µE light, 70% humidity in a Percival growth chamber.

Experiment-2: Comparison of the UV Tolerance of Genetically Modified *Chlorella sorokiniana* and Wild Type *Chlorella sorokiniana*

As the overexpression of SEQ ID NO. 1 is expected to result in protection against cell death, resistance of *Chlorella sorokiniana* to UV induced cell death was performed.

The genetically modified *Chlorella sorokiniana* CCAP 211/132 cells obtained in experiment 1 and wild type *Chlorella sorokiniana* cells were subjected to a UV dose of 250000µJ/$cm^2$ using CL-1000 UV crosslinker and the cultures were kept in dark for 24 hours, later, the cultures were exposed to light (2000 lux) in 12 h light/12 h dark cycles in the culture rack. The growth was monitored for 2 weeks and the optical density (OD) of the cultures was taken at 750 nm.

Figure 3A:
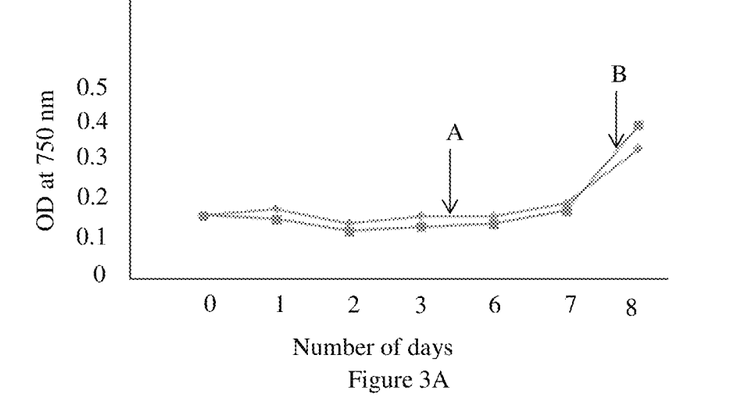
FIG. 3A represents a graph displaying the comparison of UV recovery for the wild type *Chlorella sorokiniana* and genetically modified *Chlorella sorokiniana* CCAP 211/132.
Figure 3B:
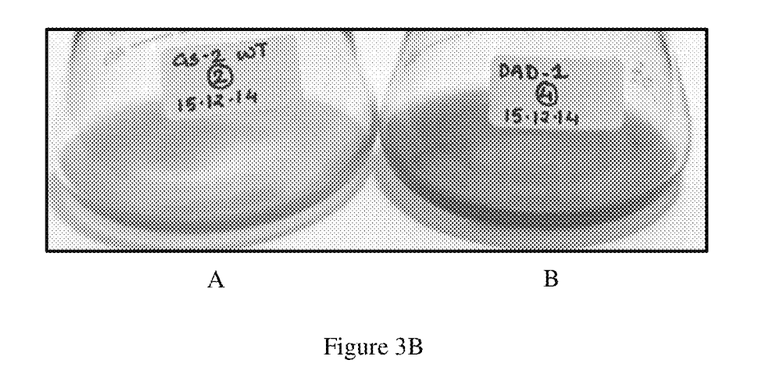
FIG. 3B illustrates the UV recovery of the wild type *Chlorella sorokiniana* and genetically modified *Chlorella sorokiniana* CCAP 211/132.
Figure 3C:
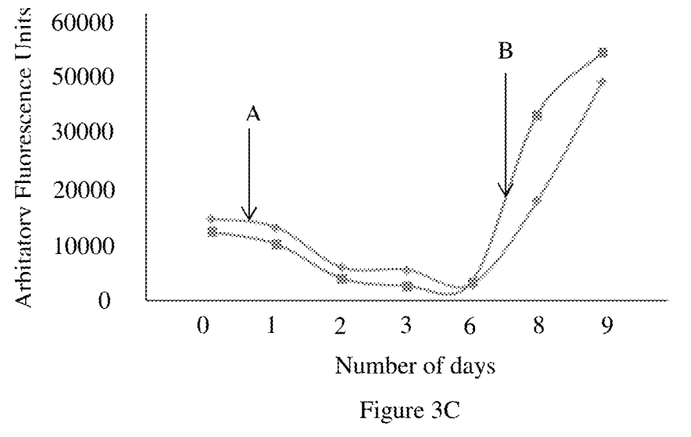
FIG. 3C represents a graph displaying the comparison of the Chlorophyll a—Fluorescence for the wild type *Chlorella sorokiniana* and genetically modified *Chlorella sorokiniana* CCAP 211/132.

A higher OD was observed for the genetically modified *Chlorella sorokiniana* CCAP 211/132 at Day 8 (after recovery from the UV stress) as compared to the wild type, as illustrated in FIG. 3A (wherein A represents wild type *Chlorella sorokiniana* and B represents genetically modified *Chlorella sorokiniana* CCAP 211/132). Since, dead cells can also contribute to OD, and give false results, the chlorophyll content of the genetically modified *Chlorella sorokiniana* CCAP 211/132 and the wild type *Chlorella sorokiniana* was measured. It was observed that the genetically modified *Chlorella sorokiniana* CCAP 211/132 had significantly higher chlorophyll than the wild type at Day 8 (after recovery from the UV stress). This is supported by FIG. 3C (wherein A represents wild type *Chlorella sorokiniana* and B represents genetically modified *Chlorella sorokiniana* CCAP 211/132) which illustrates the chlorophyll a—fluorescence and it is clearly seen from FIG. 3C that there is a significant increase in the fluorescence for the genetically modified *Chlorella sorokiniana* CCAP 211/132 from day 8 onwards. It was also visually observed that the culture of the genetically modified *Chlorella sorokiniana* CCAP 211/132 was much greener as compared to the culture of the wild type *Chlorella sorokiniana* as illustrated in FIG. 3B (wherein A represents wild type *Chlorella sorokiniana* and B represents genetically modified *Chlorella sorokiniana* CCAP 211/132). It is clearly demonstrated from the above observations that the genetically modified *Chlorella sorokiniana* CCAP 211/132 exhibited better stress tolerance to UV which is evident in the higher OD, higher fluorescence and greener culture as compared to the wild type *Chlorella sorokiniana*.

Experiment 3: Comparison of the Carrying Capacity, Clumping and Biomass of Genetically Modified *Chlorella sorokiniana* and Wild Type *Chlorella sorokiniana*

Figure 4:
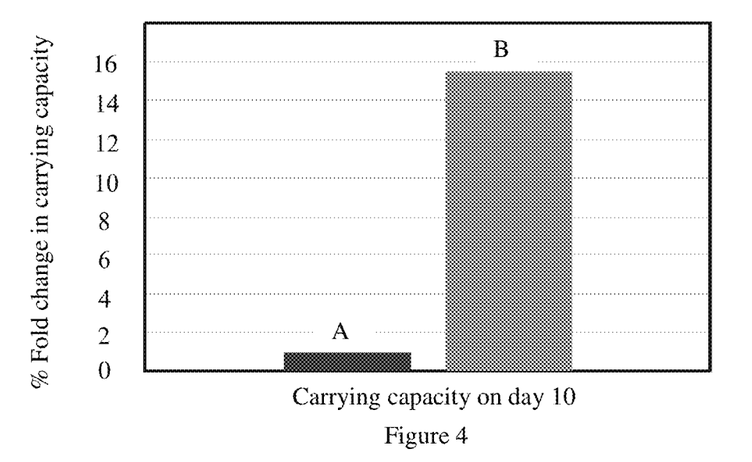
FIG. 4 represents a graph displaying the comparison of carrying capacity of wild type *Chlorella sorokiniana* and genetically modified *Chlorella sorokiniana* CCAP 211/132.

Genetically modified *Chlorella sorokiniana* CCAP 211/132 obtained in experiment 1 and wild type *Chlorella sorokiniana* were grown at 25° C., 67% humidity, 2% $CO_2$ with continuous shaking (Kuhner shaker, 100 rpm). After suitable growth was obtained for both wild type and the genetically modified *Chlorella sorokiniana*, they were transferred to 4% Salt Urea Phosphoric Acid (UPA) on a Kuhner shaker and 4% Salt UPA in Percival growth chamber (2% $CO_2$ and 450 µE light, 70% humidity). The growth was monitored for 2 weeks. The results obtained are represented in FIG. 4, where the x-axis represents the carrying capacity on day 10 and the y-axis represents the % fold change in carrying capacity the genetically modified *Chlorella sorokiniana* CCAP 211/132 on day 10 compared to the wild type *Chlorella sorokiniana*.

Figure 5:
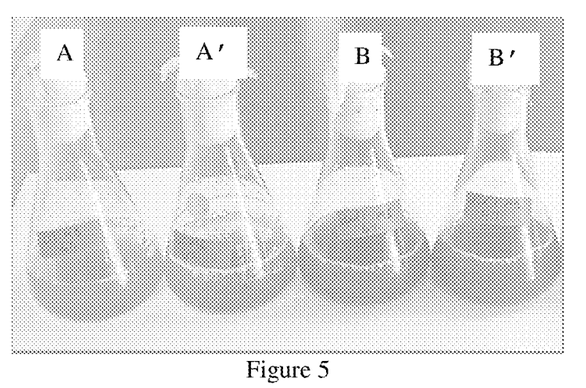
FIG. 5 illustrates the qualitative comparison of clumping for the wild type *Chlorella sorokiniana* and genetically modified *Chlorella sorokiniana* CCAP 211/132.

Carrying capacity is the maximum population size of a species possible in a given environment without gross changes in the cellular integrity or morphology. The respective fold increase in growth of the wild type *Chlorella sorokiniana* and genetically modified *Chlorella sorokiniana* CCAP 211/132 from day 1 to day 10 was calculated and normalised it with wild type *Chlorella sorokiniana* growth on day 10. After 2 weeks of growth, an increase in the carrying capacity by 15% for the genetically modified *Chlorella sorokiniana* was observed as compared to the wild type *Chlorella sorokiniana*, as depicted in FIG. 4, wherein A represents wild type *Chlorella sorokiniana* and B represents genetically modified *Chlorella sorokiniana* CCAP 211/132. Further, on visual detection, it was observed that the wild type *Chlorella sorokiniana* exhibited clump formation which was absent in the genetically modified *Chlorella sorokiniana* CCAP 211/132, as illustrated in FIG. 5 (wherein A and A' represent wild type *Chlorella sorokiniana* and B and B' represent genetically modified *Chlorella sorokiniana* CCAP 211/132. It is seen from FIG. 4 that the culture of the genetically modified *Chlorella sorokiniana* CCAP 211/132 is darker green as compared to that of the culture of the wild type *Chlorella sorokiniana*, demonstrating the reduced clumping.

Figure 6:
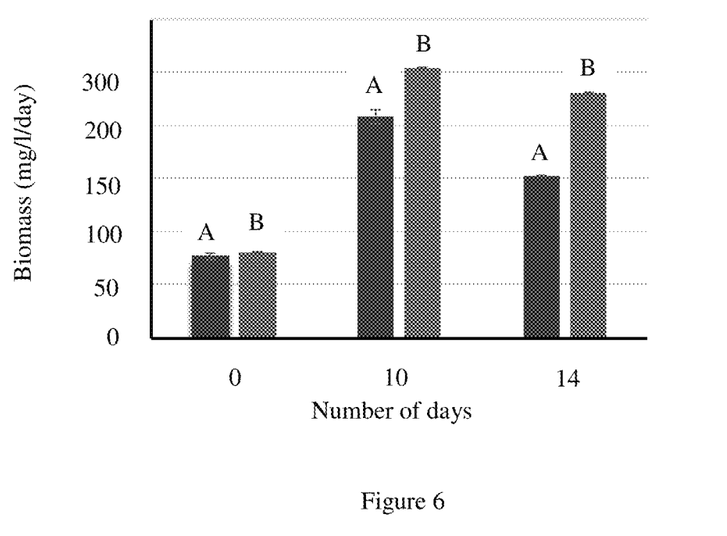
FIG. 6 represents a graph displaying the comparison of biomass production of wild type *Chlorella sorokiniana* and genetically modified *Chlorella sorokiniana* CCAP 211/132.

The genetically modified *Chlorella sorokiniana* CCAP 211/132 exhibited significant increase in growth upon high light exposure. Also, an increase in the biomass of the genetically modified *Chlorella sorokiniana* CCAP 211/132 was observed during the later phase of growth as compared to the wild type *Chlorella sorokiniana* as depicted in FIG. 6, wherein A is the wild type *Chlorella sorokiniana* and B is the genetically modified *Chlorella sorokiniana* CCAP 211/132. It is seen from FIG. 6 that the biomass increases by 21% and 51% on day 10 and day 14, respectively for the genetically modified *Chlorella sorokiniana* CCAP 211/132 as compared to that of the wild type *Chlorella sorokiniana*.

The overexpression of SEQ ID NO. 1 by the genetically modified *Chlorella sorokiniana* CCAP 211/132 arrests cell death during the later phases of growth and thereby results in increased biomass production. Also, the overexpression of SEQ ID NO. 1 confers increased stress tolerance to the genetically modified *Chlorella sorokiniana* CCAP 211/132. Thus, the genetically modified *Chlorella sorokiniana* CCAP 211/132 of the present disclosure can be used for large scale production of industrially important products, such as biofuel.

Technical Advancements

The present disclosure described herein above has several technical advantages including, but not limited to, the realization of genetically modified *Chlorella sorokiniana* CCAP 211/132 overexpressing SEQ ID NO. 1. The genetically modified *Chlorella sorokiniana* CCAP 211/132 is characterized by increased carrying capacity, reduced clumping, and increased biomass as compared to the wild type *Chlorella sorokiniana*. Further, the genetically modified *Chlorella sorokiniana* CCAP 211/132 exhibits increased stress tolerance to ultraviolet light and high light intensity, as compared to the wild type *Chlorella sorokiniana*.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. Genetically modified *Chlorella sorokiniana* having Accession Number CCAP 211/132.

2. The genetically modified *Chlorella sorokiniana* as claimed in claim 1, wherein the sequence as set forth in SEQ ID NO. 1 is overexpressed in wild type *Chlorella sorokiniana* to obtain said genetically modified *Chlorella sorokiniana*.

3. The genetically modified *Chlorella sorokiniana* as claimed in claim 1, wherein said genetically modified *Chlorella sorokiniana* is characterized by increased biomass, increased carrying capacity, reduced clumping, and increased stress tolerance to ultraviolet light and high light intensity as compared to wild type *Chlorella sorokiniana*.

4. The genetically modified *Chlorella sorokiniana* as claimed in claim 2, wherein said DAD1 gene is obtained from *Chlamydomonas reinhardtii* NW_001843471 from which the sequence as set forth in SEQ ID NO. 1 is identified and is codon-optimized for *Chlorella sorokiniana*.

5. A method of genetically modifying wild type *Chlorella sorokiniana* to obtain genetically modified *Chlorella sorokiniana* having Accession Number CCAP 211/132 as claimed in claim 1, said method comprising the following steps:

a. obtaining at least one copy of DAD1 gene from *Chlamydomonas reinhardtii* NW_001843471 and identifying the sequence as set forth in SEQ ID NO. 1;

b. isolating said SEQ ID NO. 1 from said DAD1 gene and cloning it in a vector, wherein said SEQ ID NO. 1 is codon-optimized for *Chlorella sorokiniana*; and c. introducing said vector containing said sequence as set forth in SEQ ID NO. 1 into wild type *Chlorella sorokiniana* and growing on a medium containing a selective agent under conducive conditions to facilitate the overexpression of said sequence as set forth in SEQ ID NO. 1 to obtain said genetically modified *Chlorella sorokiniana* having Accession Number CCAP 211/132.

6. The method as claimed in claim 5, wherein said vector is pChlamy 1.

7. The method as claimed in claim 5, wherein said selective agent is hygromycin.

8. The method as claimed in claim 5, wherein the step of cloning is carried out by a technique selected from the group consisting of transposon-mediated insertion, electroporation, magnetophoresis, microinjection, particle inflow gun bombardment, transfection, heat shock transfection, nucleofection transfection, delivery via liposomes and microinjection.

* * * * *

SEQUENCE LISTING

```
<160> NUMBER OF SEQ ID NOS: 1

<210> SEQ ID NO 1
<211> LENGTH: 599
<212> TYPE: DNA
<213> ORGANISM: Chlorella sorokiniana

<400> SEQUENCE: 1
gattcgaggt accatacatg ctcgccgaga tcgtgaaggc gttctcggac gagtacaaga      60
agactccagt ccgtgtgaag gttctggatg cgttcctagt ctacgcactg gcgactgcgg     120
cggttcagtt cgcgtacatg ctgctggtgg ggacgttccc cttcaacgcg ttcctggctg     180
```

-continued

```
gcttcctttc gtgcgtgggc ttcttcgccc tgactgtgtg cctgcgcatg caagtggacc    240
cagccaacaa ggagttctcg gggatatcgc ccgagcgcgc cttcgccgac tactgcctgg    300
ccaacctggt gctgcacctt gtggtctgga actacatggg ctgaccgctc cgtgtaaatg    360
gaggcgctcg ttgatctgag ccttgccccc tgacgaacgg cggtggatgg aagatactgc    420
tctcaagtgc tgaagcggta gcttagctcc ccgtttcgtg ctgatcagtc tttttcaaca    480
cgtaaaaagc ggaggagttt tgcaattttg ttggttgtaa cgatcctccg ttgattttgg    540
cctctttctc catgggcggg ctgggcgtat ttgaagcggc cgccatatga ttcgaatgt     599
```